(12) United States Patent
Akiyama et al.

(10) Patent No.: US 11,384,957 B2
(45) Date of Patent: Jul. 12, 2022

(54) DRAIN PAN, DRAIN PAN UNIT, AND AIR CONDITIONER

(71) Applicant: DAIKIN INDUSTRIES, LTD., Osaka (JP)

(72) Inventors: Ryuuji Akiyama, Osaka (JP); Kei Suzumura, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 17/376,499

(22) Filed: Jul. 15, 2021

(65) Prior Publication Data

US 2021/0341173 A1    Nov. 4, 2021

Related U.S. Application Data

(63) Continuation of application No. PCT/JP2020/003766, filed on Jan. 31, 2020.

(30) Foreign Application Priority Data

Feb. 22, 2019    (JP) .............................. JP2019-030394

(51) Int. Cl.
*F24F 13/22* (2006.01)
*A61L 2/10* (2006.01)

(52) U.S. Cl.
CPC .............. *F24F 13/222* (2013.01); *A61L 2/10* (2013.01); *F24F 2013/228* (2013.01)

(58) Field of Classification Search
CPC ........ F24F 13/22; F24F 2013/228; F24F 8/22; A61L 2/10; A61L 2/08; F25D 21/14
See application file for complete search history.

(56) References Cited

U.S. PATENT DOCUMENTS

| 5,755,103 A | * | 5/1998 | Na | F24F 1/0076 62/264 |
|---|---|---|---|---|
| 2006/0255291 A1 | * | 11/2006 | Harris | A61L 2/10 250/455.11 |
| 2015/0212252 A1 | * | 7/2015 | Sakamoto | G02B 6/0055 362/611 |
| 2020/0248924 A1 | * | 8/2020 | Suzuki | F24F 11/49 |

FOREIGN PATENT DOCUMENTS

| CN | 104515278 A | | 4/2015 |
|---|---|---|---|
| JP | 2007-23683 A | | 2/2007 |
| JP | 2007023683 A | * | 2/2007 |

(Continued)

OTHER PUBLICATIONS

International Search Report, issued in PCT/JP2020/003766, dated Apr. 7, 2020.

(Continued)

*Primary Examiner* — Elizabeth J Martin
(74) *Attorney, Agent, or Firm* — Birch, Stewart, Kolasch & Birch, LLP

(57) ABSTRACT

A drain pan includes a light-transmissive member forming at least part of the drain pan and is for transmitting ultraviolet light emitted from a light source. The light-transmissive member has a light-emitting surface that is exposed to the inside of the drain pan and from which ultraviolet light that has been transmitted through the light-transmissive member is emitted.

11 Claims, 5 Drawing Sheets

(56) References Cited

FOREIGN PATENT DOCUMENTS

| JP | 2013-160438 A | 8/2013 |
|----|---------------|--------|
| JP | 2016-35369 A  | 3/2016 |
| JP | 2016-200290 A | 12/2016 |
| JP | 2017-133700 A | 8/2017 |
| JP | 2018-155466 A | 10/2018 |

OTHER PUBLICATIONS

International Preliminary Report on Patentability and English translation of the Written Opinion of the International Searching Authority (Forms PCT/IB/338, PCT/IB/373 and PCT/ISA/237) for International Application No. PCT/JP2020/003766, dated Sep. 2, 2021.
Extended European Search Report dated Jan. 20, 2022 in counterpart European Patent Application No. 20759414.4.

\* cited by examiner

US 11,384,957 B2

DRAIN PAN, DRAIN PAN UNIT, AND AIR CONDITIONER

CROSS REFERENCE TO RELATED APPLICATIONS

This application is a Continuation of PCT International Application No. PCT/JP2020/003766, filed on Jan. 31, 2020, which claims priority under 35 U.S.C. 119(a) to Patent Application No. 2019-030394, filed in Japan on Feb. 22, 2019, all of which are hereby expressly incorporated by reference into the present application.

TECHNICAL FIELD

The present disclosure relates to a drain pan, a drain pan unit, and an air conditioner.

BACKGROUND ART

Patent Document 1 discloses an air conditioner including a drain pan. In the air conditioner, the drain pan is disposed below a heat exchanger of an indoor unit. The drain pan receives condensed water generated near the heat exchanger.

CITATION LIST

Patent Document

Patent Document 1: Japanese Unexamined Patent Publication No. 2013-160438

SUMMARY

A first aspect of the present disclosure is directed to a drain pan for receiving water. The drain pan includes: a light-transmissive member (T) forming at least part of the drain pan (41) and is for transmitting ultraviolet light emitted from a light source (80). The light-transmissive member (T) has a light-emitting surface (61) that is exposed to an inside of the drain pan (41) and from which ultraviolet light that has been transmitted through the light-transmissive member (T) is emitted.

DESCRIPTION OF EMBODIMENTS

Embodiments of the present disclosure will be described below with reference to the drawings. The following embodiments are merely exemplary ones in nature, and are not intended to limit the scope, application, or uses of the invention.

A drain pan (41) according to the present disclosure is included in a drain pan unit (40). The drain pan unit (40) is used for an air conditioner (1).

<Configuration of Air Conditioner>

Figure 1:
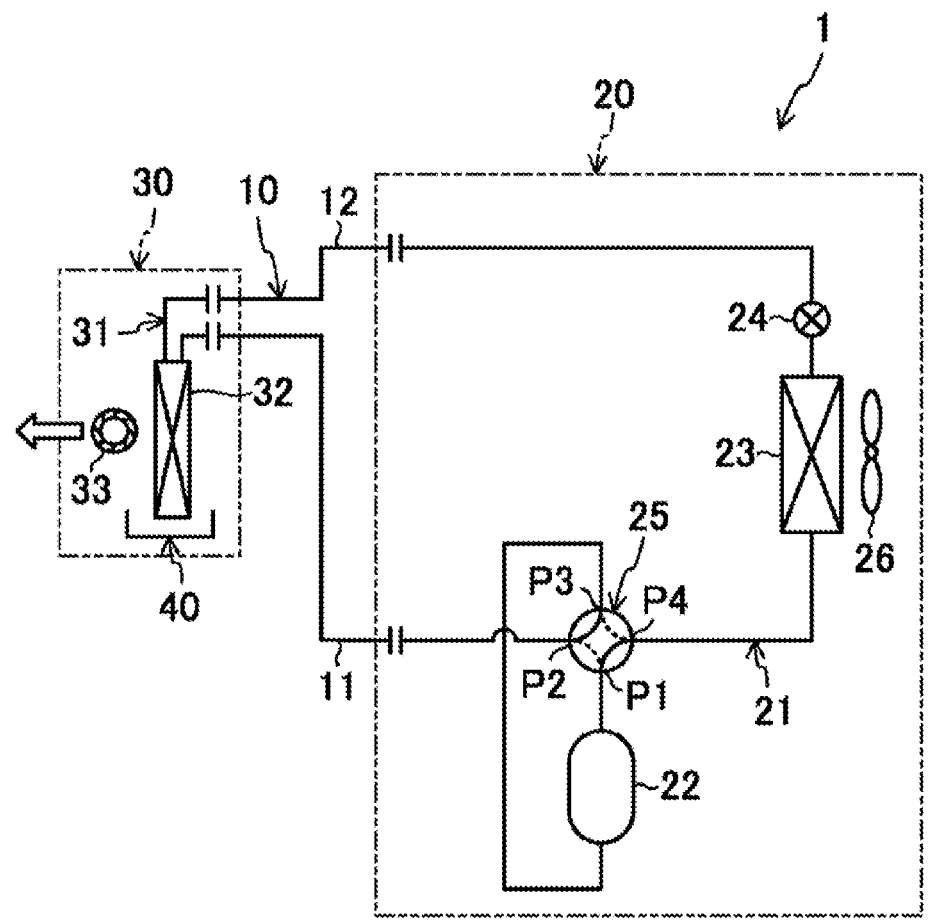
FIG. 1 is a piping system diagram illustrating a schematic configuration of an air conditioner according to an embodiment.

As schematically illustrated in FIG. 1, the air conditioner (1) includes one outdoor unit (20) and one indoor unit (30), and is of a so-called pair type. The outdoor unit (20) is placed outside. The indoor unit (30) is placed inside. The indoor unit (30) is of, for example, a wall-hanging type to be attached to a wall surface.

The air conditioner (1) further includes a refrigerant circuit (10). The refrigerant circuit (10) is filled with a refrigerant which circulates to perform a refrigeration cycle. The refrigerant circuit (10) includes an outdoor circuit (21) and an indoor circuit (31). The outdoor circuit (21) and the indoor circuit (31) are connected to each other via two connection pipes (11, 12).

The outdoor circuit (21) includes a compressor (22), an outdoor heat exchanger (23), an expansion valve (24), and a four-way switching valve (25). The compressor (22) compresses a refrigerant sucked thereinto and discharges the compressed refrigerant. The outdoor heat exchanger (23) exchanges heat between the refrigerant and outdoor air. An outdoor fan (26) is installed near the outdoor heat exchanger (23). The outdoor fan (26) transfers outdoor air. The transferred air passes through the outdoor heat exchanger (23). The expansion valve (24) is a control valve having a variable opening degree. The expansion valve (24) is configured as an electronic expansion valve. The expansion valve (24) may be connected to the liquid line of the indoor circuit (31).

The four-way switching valve (25) has a first port (P1), a second port (P2), a third port (P3), and a fourth port (P4). The first port (P1) communicates with the outlet of the compressor (22). The second port (P2) communicates with a gas-side connection pipe (11). The third port (P3) communicates with the inlet of the compressor (22). The fourth port (P4) communicates with the gas end of the outdoor heat exchanger (23). The four-way switching valve (25) switches between a first state (the state indicated by solid curves in FIG. 1) and a second state (the state indicated by broken curves in FIG. 1). The four-way switching valve (25) in the first state makes the first and fourth ports (P1) and (P4) communicate with each other, and the second and third ports (P2) and (P3) communicate with each other. The four-way switching valve (25) in the second state makes the first and second ports (P1) and (P2) communicate with each other, and the third and fourth ports (P3) and (P4) communicate with each other.

The indoor circuit (31) includes an indoor heat exchanger (32). The indoor heat exchanger (32) exchanges heat between the refrigerant and indoor air. An indoor fan (33) is placed near the indoor heat exchanger (32). The indoor fan (33) transfers indoor air. The transferred indoor air passes through the indoor heat exchanger (32). The drain pan unit (40) is disposed below the indoor heat exchanger (32).

—Operation—

The air conditioner (1) performs a cooling operation and a heating operation.

<Cooling Operation>

In the cooling operation, the four-way switching valve (25) is brought into the first state. The refrigerant compressed in the compressor (22) dissipates heat or is condensed in the outdoor heat exchanger (23). The refrigerant that has dissipated heat and has been condensed is decompressed by the expansion valve (24), and then flows through the indoor heat exchanger (32). In the indoor heat exchanger (32), the refrigerant absorbs heat from indoor air to evaporate. The indoor air cooled by the indoor heat exchanger (32) is supplied into an indoor space. The evaporated refrigerant is sucked into the compressor (22). In the cooling operation, condensed water is produced near the indoor heat exchanger (32). The condensed water is received inside the drain pan (41).

<Heating Operation>

In the heating operation, the four-way switching valve (25) is brought into the second state. The refrigerant compressed in the compressor (22) flows through the indoor heat exchanger (32). In the indoor heat exchanger (32), the refrigerant dissipates heat to indoor air to condense. The indoor air heated by the indoor heat exchanger (32) is supplied into the indoor space. The condensed refrigerant is decompressed by the expansion valve (24), and then evaporates in the outdoor heat exchanger (23). The evaporated refrigerant is sucked into the compressor (22).

<Drain Pan Unit>

Figure 2:
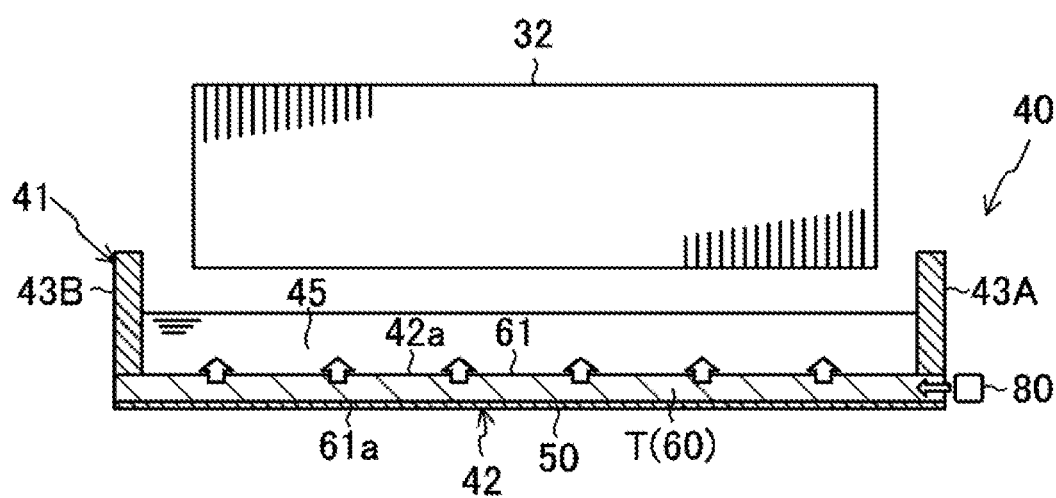
FIG. 2 is a longitudinal sectional view illustrating a schematic configuration of a drain pan unit according to an embodiment.
Figure 3:
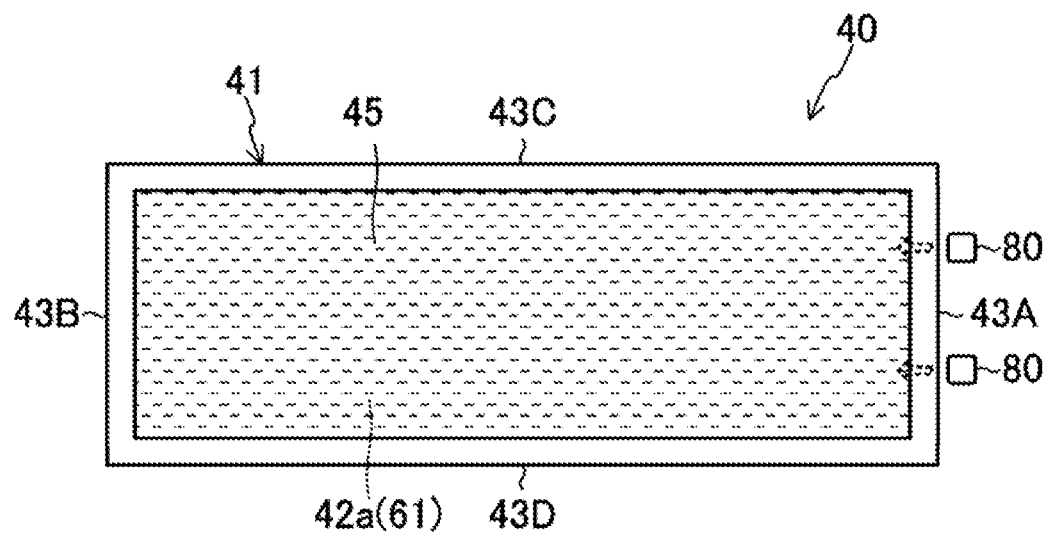
FIG. 3 is a plan view illustrating the schematic configuration of the drain pan unit according to the embodiment.
Figure 4:
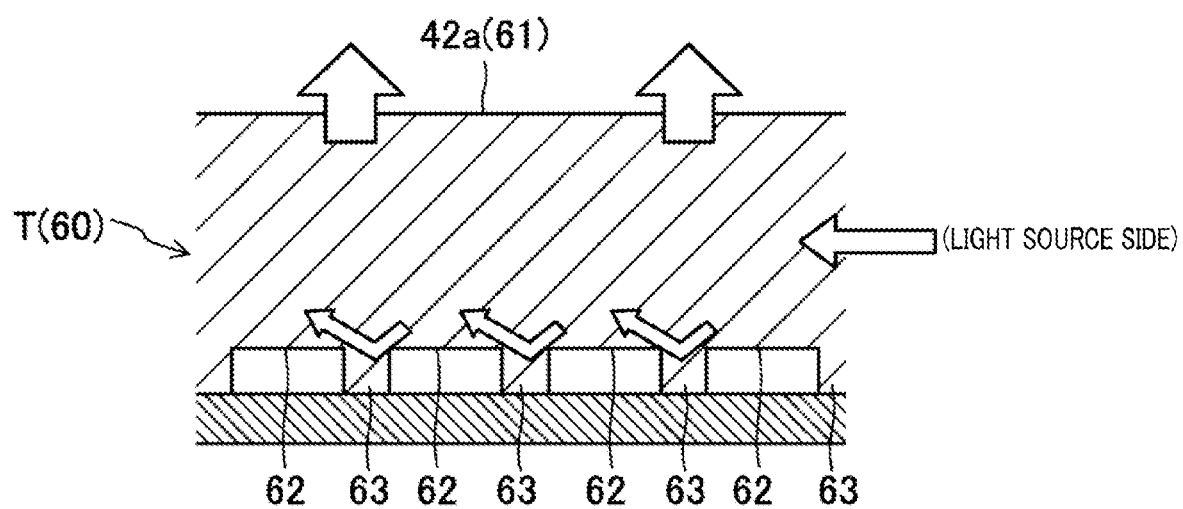
FIG. 4 is an enlarged longitudinal sectional view schematically illustrating a light-transmissive member of the drain pan unit according to the embodiment.

The air conditioner (1) includes the drain pan unit (40). The drain pan unit (40) of this embodiment is disposed below the indoor heat exchanger (32). As illustrated in FIGS. 2 and 3, the drain pan unit (40) includes the drain pan (41) and two light sources (80). The light sources (80) of this embodiment are disposed on a side of the drain pan (41).

The drain pan (41) constitutes a tray for receiving water. The drain pan (41) includes a bottom wall (42) and four side walls (43A, 43B, 43C, 43D). The bottom wall (42) constitutes a bottom portion of the drain pan (41). The bottom wall (42) has a horizontally oriented rectangular shape. The four side walls (43A, 43B, 43C, 43D) are arranged around the bottom wall (42). The side walls (43A, 43B, 43C, 43D) each extend upward from an associated one of the edges of the bottom wall (42). The first side wall (43A) is provided at one end of the bottom wall (42) in the longitudinal direction of the bottom wall (42). The second side wall (43B) is provided at the other end of the bottom wall (42) in the longitudinal direction of the bottom wall (42). The third side wall (43C) is provided at one end of the bottom wall (42) in the width direction of the bottom wall (42). The fourth side wall (43D) is provided at the other end of the bottom wall (42) in the width direction of the bottom wall (42). These four side walls (43A, 43B, 43C, 43D) have a rectangular frame shape in plan view. The drain pan (41) has an internal space (45) defined by the bottom wall (42) and the four side walls (43A, 43B, 43C, 43D). The internal space (45) is used to receive water. The internal space (45) can store condensed water.

The bottom wall (42) of this embodiment includes a reflector (50) and a light guide member (60). The reflector (50) and the light guide member (60) have the same rectangular shape in plan view. The reflector (50) is disposed below the light guide member (60). The reflector (50) and the light guide member (60) are placed one over the other in their thickness direction. In other words, the reflector (50) overlaps with a surface (61a) of the light guide member (60) opposite to a light-emitting surface (61) thereof. The reflector (50) has a smaller thickness than the light guide member (60).

The reflector (50) is made of a metal material, such as aluminum or stainless steel. At least an upper surface of the reflector (50) is configured as a reflection surface. In one preferred embodiment, the reflector (50) is made of a material that reflects light toward the inside of the drain pan (41).

The light guide member (60) constitutes a light-transmissive member (T) that transmits ultraviolet light. The light-transmissive member (T) of this embodiment is made of quartz. The light-transmissive member (T) may be a light-transmissive resin material. Examples of the light-transmissive resin material include an acrylic resin, a silicone resin, and an epoxy resin.

At least a portion of the light guide member (60) is exposed to the internal space (45) of the drain pan (41). In other words, the light guide member (60) has an exposed surface exposed to the inside of the drain pan (41). This exposed surface constitutes the light-emitting surface (61) from which ultraviolet light is emitted. The light-emitting surface (61) constitutes a bottom surface (42a) of the drain pan (41).

The light sources (80) are each configured as an ultraviolet light generator that emits ultraviolet light. The light sources (80) of this embodiment are disposed outside the drain pan (41). The light sources (80) are disposed on a side of the light guide member (60) of the drain pan (41) and near the light guide member (60). Specifically, the light sources (80) are close to a portion of the light guide member (60) located under the first side wall (43A).

As illustrated in FIG. 3, in this embodiment, the two light sources (80) are disposed near the light guide member (60). The number of the light sources (80) is merely an example, and may be one, or three or more. In one preferred embodiment, the light sources (80) are spaced uniformly. The light sources (80) apply ultraviolet rays toward the inside of the light guide member (60). Ultraviolet light emitted from the light sources (80) is applied toward the light guide member (60).

The light guide member (60) constitutes a light-guiding plate that guides ultraviolet light incident thereon in a predetermined direction. The light guide member (60) has the property of directing the ultraviolet light incident thereon toward the light-emitting surface (61). A plurality of recesses (62) and a plurality of protrusions (63) are arranged on a lower surface of the light guide member (60). The ultraviolet light that is laterally transmitted through the inside of the light guide member (60) is reflected off the recesses (62) and the protrusions (63). The reflected ultraviolet light travels toward the inside of the drain pan (41). In addition, the ultraviolet light traveling toward the lower side of the light guide member (60) is reflected off the reflector (50) to travel toward the inside of the drain pan (41). Such a configuration of the drain pan (41) allows ultraviolet light to be emitted from the light-emitting surface (61) of the light guide member (60) toward the inside of the drain pan (41).

—Purification with Ultraviolet Light—

The light sources (80) turned on allow ultraviolet light generated from the light sources (80) to be laterally transmitted through the inside of the light guide member (60). As described above, the direction of the ultraviolet light is changed by the recesses (62), the protrusions (63), and the reflector (50). Thus, the ultraviolet light travels toward the bottom surface (42a) of the drain pan (41). The ultraviolet light is applied from the light-emitting surface (61) of the light guide member (60) to the inside of the drain pan (41). In other words, the ultraviolet light is applied from the bottom surface (42a) of the drain pan (41) to the inside of the drain pan (41). As a result, the bactericidal action of the ultraviolet light reduces propagation of bacteria inside the drain pan (41).

Advantages of Embodiment

In this embodiment, the drain pan (41) for receiving water includes the light-transmissive member (T) forming at least part of the drain pan (41) and is for transmitting ultraviolet light emitted from the light sources (80). The light-transmissive member (T) is exposed to the inside of the drain pan (41), and has the light-emitting surface (61) from which the ultraviolet light that has been transmitted through the light-transmissive member (T) is emitted.

This feature enables the ultraviolet light generated from the light sources (80) to be emitted from the light-emitting surface (61) inside the drain pan (41). The drain pan (41) internally having the light-emitting surface (61) from which ultraviolet light is emitted enables the bactericidal action on the light-emitting surface (61) to be enhanced, and mold and microbial films on the light-emitting surface (61) to be reduced. This avoids clogging of, for example, a pump or a drain port, and reduces unpleasant odors.

In this embodiment, the light-transmissive member (T) is provided on or as the bottom wall (42) of the drain pan (41), and the light-emitting surface (61) of the light-transmissive member (T) constitutes the bottom surface (42a) of the drain pan (41).

This feature enables ultraviolet rays to be emitted from the bottom surface (42a) of the drain pan (41). This improves the bactericidal action on the bottom surface (42a) of the drain pan (41). In addition, the light-transmissive member (T) serves also as the bottom wall (42) of the drain pan (41). This reduces the number of components.

In this embodiment, the light sources (80) are disposed on a side of the light-transmissive member (T), which is the light guide member (60) that guides incident ultraviolet light from the side of the light-transmissive member (T) toward the light-emitting surface (61).

This feature enables ultraviolet light to be applied from the light-emitting surface (61), which is the bottom surface (42a) of the drain pan (41), while the light sources (80) are disposed on the side of the light guide member (60). This arrangement of the light sources (80) substantially prevents condensed water from splashing on the light sources (80). This arrangement also reduces the space for installation of the light sources (80) in the height direction of the light sources (80).

In this embodiment, the reflector (50) is arranged to overlap with the surface (61a) of the light guide member (60) opposite to the light-emitting surface (61) to reflect ultraviolet light.

This feature substantially prevents ultraviolet light being transmitted through the inside of the light guide member (60) from the side thereof, from leaking downward of the light guide member (60). In addition, the ultraviolet light directed downward of the light guide member (60) is reflected upward and guided toward the light-emitting surface (61).

Variations of Embodiment

The foregoing embodiment may also be configured as the following variations.

<First Variation>

Figure 5:
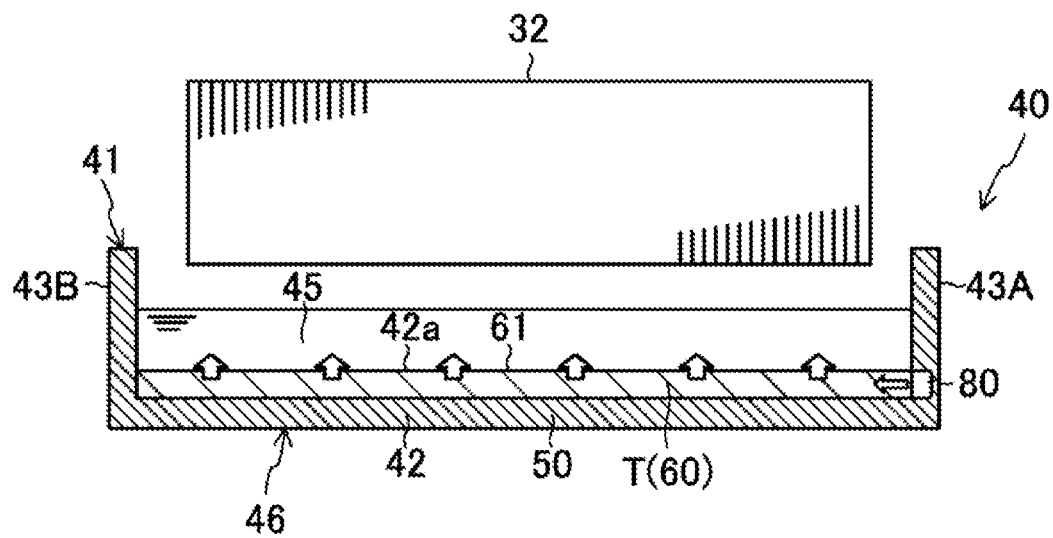
FIG. 5 is a longitudinal sectional view illustrating a schematic configuration of a drain pan unit according to a first variation.

As illustrated in FIG. 5, a drain pan (41) according to a first variation includes a drain pan body (46) and a light guide member (60) placed at the bottom of the drain pan body (46).

The drain pan body (46) is made of a metal material, such as stainless steel or aluminum. The drain pan body (46) has a dish shape or a flat box shape with its upper end open. The drain pan body (46) has four side walls (43A, 43B, 43C, 43D) just like the foregoing embodiment.

The drain pan body (46) includes a bottom plate (47) serving also as a reflector (50). The light guide member (60) is placed over the upper surface of the bottom plate (47). The bottom plate (47) and the light guide member (60) constitute a bottom wall (42) (bottom portion) of the drain pan (41). The upper surface of the light guide member (60) forms a light-emitting surface (61) exposed to the inside of the drain pan (41).

Light sources (80) of this variation are provided inside the drain pan (41). Specifically, the light sources (80) are embedded inside the first side wall (43A). The light sources (80) are disposed on a side of the light guide member (60). The light sources (80) face a lateral end of the light guide member (60). The light sources (80) apply ultraviolet light toward the light guide member (60). The light guide member (60) has a plurality of recesses (62) and a plurality of protrusions (63) just like the foregoing embodiment.

The ultraviolet light applied from the light sources (80) is transmitted through the inside of the light guide member (60). The ultraviolet light is reflected off the recesses (62) and the protrusions (63) inside the light guide member (60). In addition, the ultraviolet light is reflected off the reflector (50) serving also as the bottom plate (47). The reflected ultraviolet light changes its direction upward, and is emitted from the light-emitting surface (61) into the drain pan (41). As a result, the inside of the drain pan (41) is sterilized.

In the first variation, the bottom plate (47), which is a portion of the drain pan (41), serves also as the reflector (50). This reduces the number of components.

<Second Variation>

Figure 6:
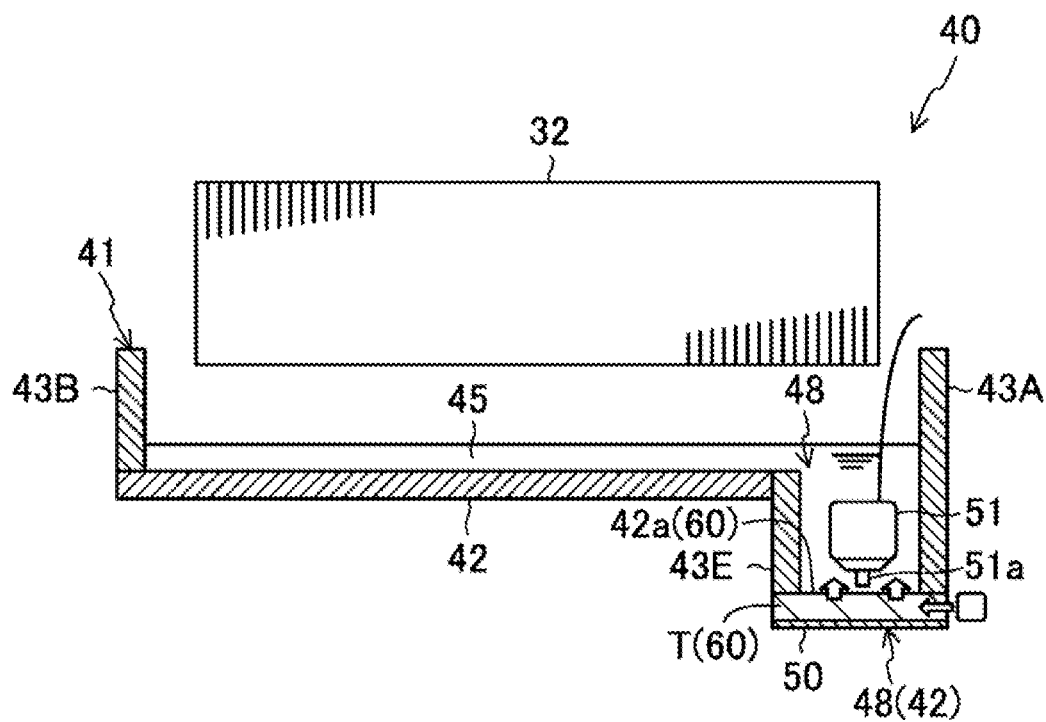
FIG. 6 is a longitudinal sectional view illustrating a schematic configuration of a drain pan unit according to a second variation.

As illustrated in FIG. 6, a bottom wall (42) of a drain pan (41) according to a second variation has a drain pan recess (48) recessed downward. The drain pan recess (48) includes a lower portion of a first side wall (43A), a fifth side wall (43E), and a recess bottom portion (48). The fifth side wall (43E) faces the first side wall (43A). The recess bottom portion (48) constitutes a bottom portion of the drain pan recess (62). A pump (51) is housed in a space defined by the first side wall (43A), the fifth side wall (43E), and the recess bottom portion (48). The pump (51) pumps water inside the drain pan (41).

In the second variation, the recess bottom portion (48) includes a light guide member (60) and a reflector (50). The reflector (50) is stacked on a lower surface of the light guide member (60). The light guide member (60) has a light-emitting surface (61) exposed to the inside of the drain pan (41). The light-emitting surface (61) constitutes a bottom surface (42a) of the drain pan recess (48) of the drain pan (41). The light-emitting surface (61) faces upward. The light-emitting surface (61) faces the pump (51). Light sources (80) are disposed outside the drain pan (41) and on a side of the recess bottom portion (48). The light sources (80) are close to the first side wall (43A).

In the second variation, the ultraviolet light applied from the light sources (80) is transmitted through the inside of the light guide member (60) of the recess bottom portion (48). The ultraviolet light is reflected off the recesses (62), the protrusions (63), and the reflector (50), and travels toward the inside of the drain pan (41). As a result, the ultraviolet light is emitted from the bottom surface (42a) (i.e., the light-emitting surface (61)) of the recess bottom portion (48). The ultraviolet light emitted from the light-emitting surface (61) is used to sterilize the inside of the drain pan (41).

In the second variation, the pump (51) that sucks water in the drain pan (41) is provided, and the light-emitting surface (61) of the light-transmissive member (T) faces the pump (51).

This feature enables the ultraviolet light emitted from the light-emitting surface (61) to be applied to the pump (51). This reduces propagation of mold and microbial films around the pump (51). In particular, according to this feature, the light-emitting surface (61) faces the inlet (51a) of the pump (51). This reduces propagation of mold and microbial films around the inlet (51a). This enables reduction in clogging of the inlet (51a) of the pump (51).

<Third Variation>

Figure 7:
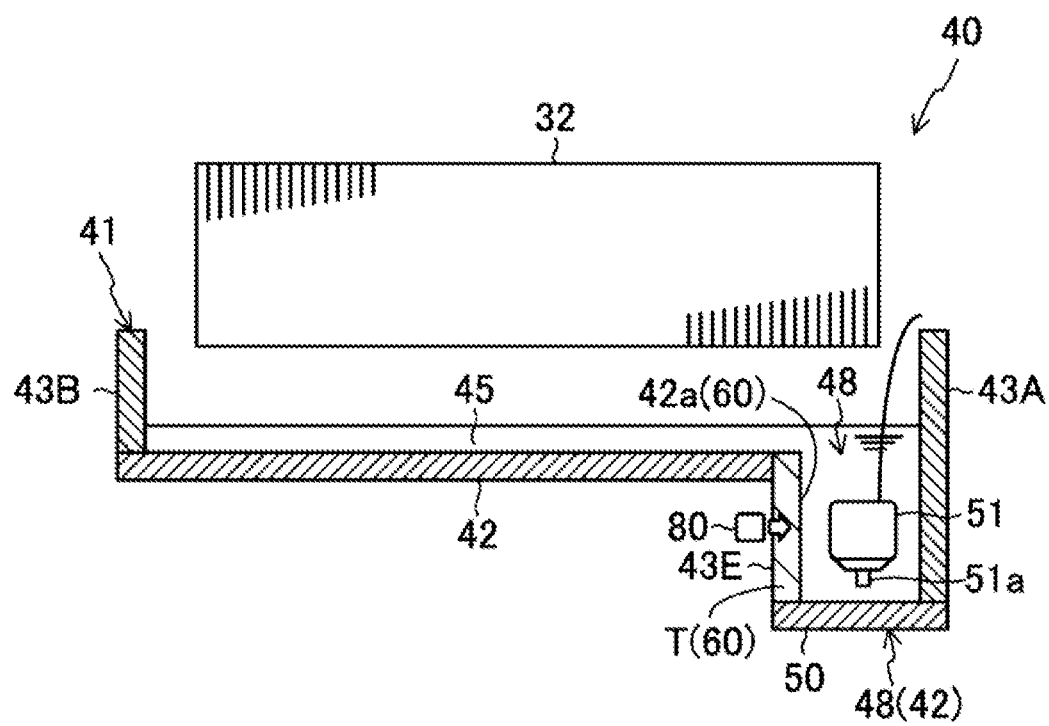
FIG. 7 is a longitudinal sectional view illustrating a schematic configuration of a drain pan unit according to a third variation.

As illustrated in FIG. 7, a bottom wall (42) of a drain pan (41) according to a third variation has a drain pan recess (48). In the third variation, a fifth side wall (43E) of the drain pan recess (48) is configured as a light-transmissive member (T). The light-transmissive member (T) does not need to be capable of changing the direction of ultraviolet light unlike the first and second embodiments. An inner side surface of the fifth side wall (43E) forms an exposed surface exposed to the inside of the drain pan (41). This exposed surface constitutes a light-emitting surface (61). The light-emitting surface (61) faces the pump (51).

Light sources (80) are disposed outside the drain pan (41) and on a side of the fifth side wall (43E). The light sources (80) are close to the fifth side wall (43E).

In the third variation, ultraviolet light applied from the light sources (80) is transmitted through the light-transmissive member (T) in the thickness direction of the light-transmissive member (T). As a result, ultraviolet light is emitted from the light-emitting surface (61) of the fifth side wall (43E). The ultraviolet light emitted from the light-emitting surface (61) is used to sterilize the inside of the drain pan (41), for example. In addition, the ultraviolet light is used to sterilize an area surrounding the drain pan (41), for example.

In the third variation, one of surfaces of the light-transmissive member (T) in the thickness direction thereof forms the light-emitting surface (61). The light sources (80) are close to the other surface of the light-transmissive member (T) in the thickness direction thereof. This minimizes the distance over which the ultraviolet light passes through the light-transmissive member (T), and increases the intensity of the ultraviolet light emitted from the light-emitting surface (61).

<Fourth Variation>

Figure 8:
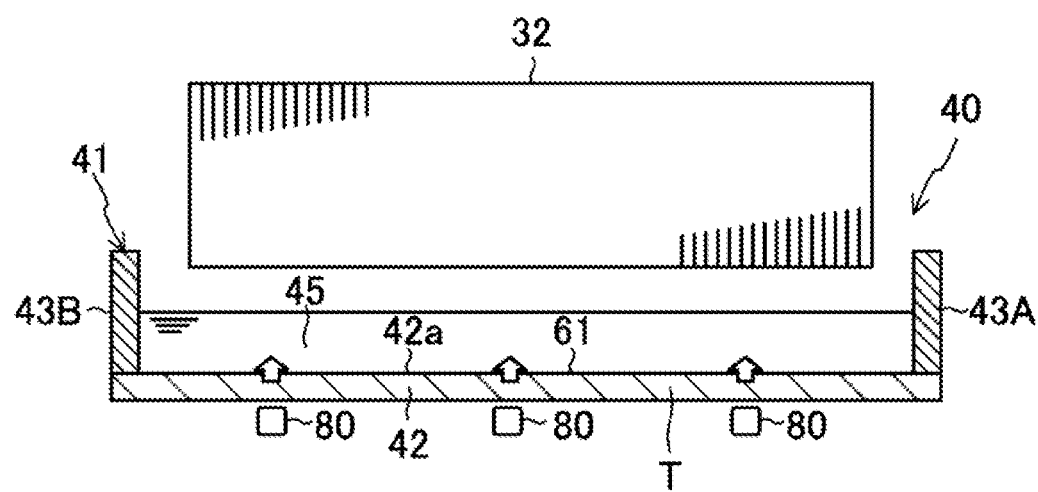
FIG. 8 is a longitudinal sectional view illustrating a schematic configuration of a drain pan unit according to a fourth variation.

As illustrated in FIG. 8, a bottom wall (42) of a drain pan (41) according to a fourth variation is configured as a light-transmissive member (T). The light-transmissive member (T) does not need to be a light guide member capable of changing the direction of ultraviolet light. An upper surface of the light-transmissive member (T) forms a light-emitting surface (61) exposed to the inside of the drain pan (41).

A plurality of light sources (80) according to the fourth variation are disposed behind the bottom wall (42) of the drain pan (41). Specifically, the drain pan (41) is disposed outside the drain pan (41) and below the bottom wall (42). The light sources (80) are close to the bottom wall (42). In this variation, the light sources (80) are arranged along the back surface of the drain pan (41).

The light sources (80) apply ultraviolet light upward toward the light-transmissive member (T). The ultraviolet light passes through the light-transmissive member (T) in the thickness direction thereof, and is emitted upward from the light-emitting surface (61). As a result, the inside of the drain pan (41) is sterilized.

In the fourth variation, the light-transmissive member (T) serves also as the bottom wall (42) of the drain pan (41). This reduces the number of components.

In the fourth variation, one of surfaces (an upper surface) of the light-transmissive member (T) in the thickness direction thereof forms the light-emitting surface (61). The light sources (80) are close to the other surface (a lower surface) of the light-transmissive member (T) in the thickness direction thereof. This minimizes the distance over which the ultraviolet light passes through the light-transmissive member (T), and increases the intensity of the ultraviolet light emitted from the light-emitting surface (61).

<Fifth Variation>

Figure 9:
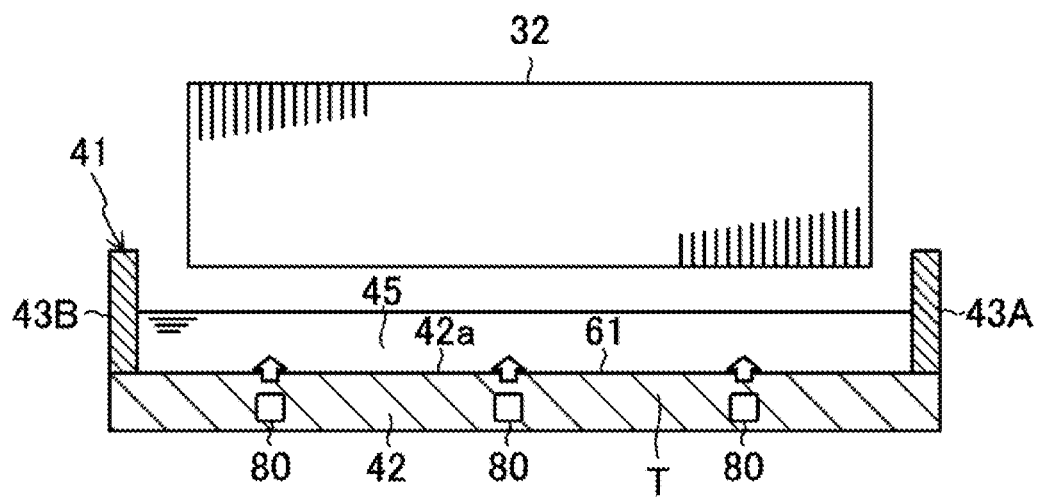
FIG. 9 is a longitudinal sectional view illustrating a schematic configuration of a drain pan unit according to a fifth variation.

As illustrated in FIG. 9, a bottom wall (42) of a drain pan (41) according to a fifth variation is configured as a light-transmissive member (T). The light-transmissive member (T) does not need to be a light guide member capable of changing the direction of ultraviolet light. An upper surface of the light-transmissive member (T) forms a light-emitting surface (61) exposed to the inside of the drain pan (41).

A plurality of light sources (80) according to the fifth variation are disposed inside the bottom wall (42) of the drain pan (41). In other words, the light sources (80) are embedded in the bottom wall (42). The light sources (80) face upward. Light is applied upward from the light sources (80).

The light sources (80) apply ultraviolet light upward toward the light-transmissive member (T). The ultraviolet light passes through the light-transmissive member (T) in the thickness direction thereof, and is emitted upward from the light-emitting surface (61). As a result, the inside of the drain pan (41) is sterilized. In this variation, the light sources (80) are arranged along the back surface of the drain pan (41).

In the fifth variation, the light-transmissive member (T) serves also as the bottom wall (42) of the drain pan (41). This reduces the number of components.

In the fifth variation, the distance from the light sources (80) to the light-emitting surface (61) is relatively short. This increases the intensity of the ultraviolet light emitted from the light-emitting surface (61).

OTHER EMBODIMENTS

All of the embodiment and variations described above may have the following configurations.

Figure 10:
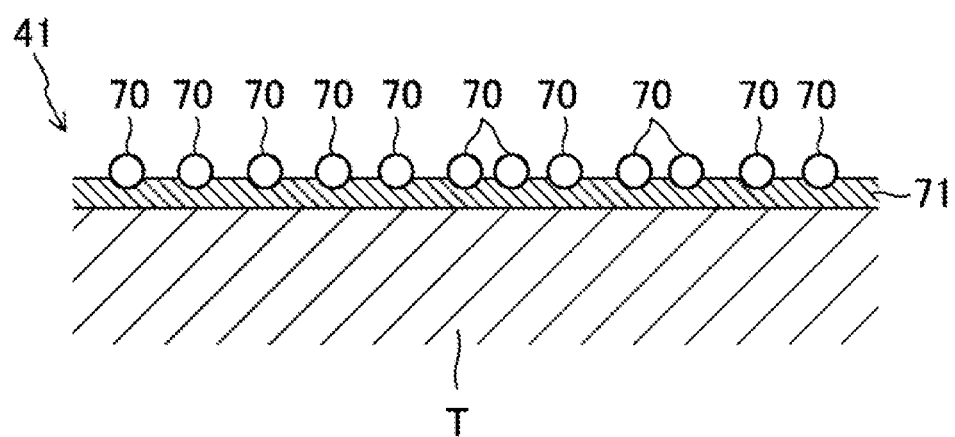
FIG. 10 is an enlarged longitudinal sectional view schematically illustrating a light-transmissive member of a drain pan unit according to another embodiment.

As illustrated in FIG. 10, the drain pan (41) may include photocatalysts (70) exposed to the inside of the drain pan (41). In one preferred embodiment, the photocatalysts (70) are provided on the light-emitting surface (61). In the example illustrated in FIG. 10, the photocatalysts (70) are supported on the light-emitting surface (61) via a thin film (71). The photocatalysts (70) are made of, for example, titanium dioxide. The photocatalysts (70) irradiated with ultraviolet light have their oxidative decomposition performance enhanced, and improve the bactericidal action.

The light-transmissive member (T) may be provided on any portion of the drain pan (41) as long as the light-transmissive member (T) has the light-emitting surface (61) exposed to the inside of the drain pan (41). The reflector (50) may be provided on any portion of the drain pan (41) as long as the reflector (50) is placed over the surface (61a) of the light-transmissive member (T) opposite to the light-emitting surface (61).

The drain pan unit (40) having the feature described above is used for the wall-hanging indoor unit (30). The drain pan unit (40) may be used for a ceiling-mounted indoor unit. The ceiling-mounted indoor unit includes a ceiling-suspended indoor unit and a ceiling-embedded indoor unit.

The drain pan unit (40) may be used for the outdoor unit (20).

The drain pan unit (40) may be used for an air conditioner having an air humidifying function. In this case, the drain pan unit (40) receives water discharged from a humidifier, such as a humidifying element.

While the embodiments and the variations thereof have been described above, it will be understood that various changes in form and details may be made without departing from the spirit and scope of the claims. The embodiment, the variations thereof, and the other embodiments may be combined and replaced with each other without deteriorating intended functions of the present disclosure. The expressions of "first," "second," and "third" described above are used to distinguish the terms to which these expressions are given, and do not limit the number and order of the terms.

INDUSTRIAL APPLICABILITY

The present disclosure is useful for a drain pan, a drain pan unit, and an air conditioner.

EXPLANATION OF REFERENCES

1 Air Conditioner
32 Heat Exchanger (Indoor Heat Exchanger)
40 Drain Pan Unit
41 Drain Pan
42 Bottom Portion
42a Bottom Surface
50 Reflector
51 Pump
60 Light Guide Member
61 Light-emitting Surface
61a Opposite Surface
70 Photocatalyst
80 Light Source

The invention claimed is:

1. A drain pan unit for an air conditioner and for receiving water, the drain pan unit comprising:
a light-transmissive member forming at least part of the drain pan unit, and is for transmitting ultraviolet light emitted from a light source,
the light-transmissive member having a light-emitting surface that is exposed to an inside of the drain pan unit and from which ultraviolet light that has been transmitted through the light-transmissive member is emitted, wherein
the light source is disposed on a side of the light-transmissive member,
the light-transmissive member is provided on or as a bottom portion of the drain pan unit,
the light-transmissive member is a light guide member that guides incident ultraviolet light from the side of the light-transmissive member toward the light-emitting surface, and
a recess and a protrusion are formed on a lower surface of the light guide member opposite to the light-emitting surface.

2. The drain pan unit of claim 1, wherein
the light-emitting surface of the light-transmissive member forms a bottom surface of the drain pan unit.

3. The drain pan unit of claim 1, further comprising:
a photocatalyst exposed to the inside of the drain pan unit.

4. The drain pan unit of claim 3, wherein
the photocatalyst is provided on the light-emitting surface.

5. The drain pan unit of claim 1, wherein
the light-transmissive member is made of quartz or a light-transmissive resin material.

6. The drain pan unit of claim 1, further comprising:
a reflector placed over a lower surface of the light guide member opposite to the light-emitting surface to reflect ultraviolet light.

7. The drain pan unit of claim 6, wherein
the reflector serves also as the drain pan unit.

8. The drain pan unit of claim 1, further comprising:
a pump configured to suck water in the drain pan unit, wherein
the light-emitting surface of the light-transmissive member faces the pump.

9. The drain pan unit of claim 1, wherein
the light source is disposed outside the light-transmissive member.

10. An air conditioner comprising:
a heat exchanger; and
a drain pan unit configured to receive water condensed in the heat exchanger,
the drain pan unit being the drain pan unit of claim 1.

11. The drain pan unit of claim 1, wherein
the light-transmissive member is situated in a position that is aligned with the light source along a longitudinal direction of the light-transmissive member.

* * * * *